United States Patent
Suddaby

(10) Patent No.: US 7,044,971 B2
(45) Date of Patent: May 16, 2006

(54) LORDOTIC FUSION IMPLANT

(76) Inventor: Loubert Suddaby, 76 Tanglewood Dr., Orchard Park, NY (US) 14127

( * ) Notice: Subject to any disclaimer, the term of this patent is extended or adjusted under 35 U.S.C. 154(b) by 68 days.

(21) Appl. No.: 10/231,306

(22) Filed: Aug. 30, 2002

(65) Prior Publication Data
US 2004/0044411 A1    Mar. 4, 2004

(51) Int. Cl.
  *A61F 2/44*    (2006.01)
(52) U.S. Cl. .................. 623/17.15; 623/17.11
(58) Field of Classification Search ............ 623/17.11, 623/17.15, 17.16; 606/61
See application file for complete search history.

(56) References Cited
U.S. PATENT DOCUMENTS

| | | | |
|---|---|---|---|
| 5,147,402 A | * | 9/1992 | Bohler et al. ............ 623/16.11 |
| 5,505,732 A | | 4/1996 | Michelson |
| 5,653,762 A | | 8/1997 | Pisharodi |
| 5,665,122 A | | 9/1997 | Kambin |
| 5,683,463 A | | 11/1997 | Godefroy et al. |
| 5,782,832 A | * | 7/1998 | Larsen et al. .................. 606/61 |
| 6,159,244 A | * | 12/2000 | Suddaby .................. 623/17.11 |
| 6,190,414 B1 | * | 2/2001 | Young et al. ............ 623/17.15 |
| 6,193,757 B1 | * | 2/2001 | Foley et al. ............. 623/17.16 |
| 6,491,724 B1 | * | 12/2002 | Ferree ..................... 623/17.11 |

FOREIGN PATENT DOCUMENTS

DE    19827515 A1 *  12/1999

* cited by examiner

*Primary Examiner*—Brian E. Pellegrino
(74) *Attorney, Agent, or Firm*—Shoemaker and Mattare

(57) ABSTRACT

An expandable intervertebral fusion implant includes a pair of shells having mating surfaces which resist shifting when the parts are assembled. The shells have opposed legs provided with teeth which permit the shells to be ratcheted outward in a non-parallel fashion after they have been placed between spinal elements.

14 Claims, 3 Drawing Sheets

LORDOTIC FUSION IMPLANT

BACKGROUND OF THE INVENTION

This invention relates to an intervertebral fusion implant. The class of implements to which this invention pertains serve to stabilize adjacent vertebral elements, thereby facilitating the development of a bony union between them and thus long term spinal stability.

Of all animals possessing a backbone, human beings are the only creatures who remain upright for significant periods of time. From an evolutionary standpoint, this erect posture has conferred a number of strategic benefits, not the least of which is freeing the upper limbs for purposes other than locomotion. From an anthropologic standpoint, it is also evident that this unique evolutionary adaptation is a relatively recent change, and as such has not benefitted from natural selection as much as have backbones held in a horizontal attitude. As a result, the stresses acting upon the human backbone (or "vertebral column"), are unique in many senses, and result in a variety of problems or disease states that are peculiar to the human species.

The human vertebral column is essentially a tower of bones held upright by fibrous bands called ligaments and contractile elements called muscles. There are seven bones in the neck or cervical region, twelve in the chest or thoracic region, and five in the low back or lumbar region. There are also five bones in the pelvic or sacral region which are normally fused together and form the back part of the pelvis. This column of bones is critical for protecting the delicate spinal cord and nerves, and for providing structural support for the entire body.

Between the vertebral bones themselves exist soft tissue structures—discs—composed of fibrous tissue and cartilage which are compressible and act as shock absorbers for sudden downward forces on the upright column. The discs allow the bones to move independently of each other, as well. The repetitive forces which act on these intervertebral discs during repetitive day-to-day activities of bending, lifting and twisting cause them to break down or degenerate over time.

Presumably because of humans' upright posture, their intervertebral discs have a high propensity to degenerate. Overt trauma, or covert trauma occurring in the course of repetitive activities disproportionately affect the more highly mobile areas of the spine. Disruption of a disc's internal architecture leads to bulging, herniation or protrusion of pieces of the disc and eventual disc space collapse. Resulting mechanical and even chemical irritation of surrounding neural elements (spinal cord and nerves) cause pain, attended by varying degrees of disability. In addition, loss of disc space height relaxes tension on the longitudinal spinal ligaments, thereby contributing to varying degrees of spinal instability such as spinal curvature.

The time-honored method of addressing the issues of neural irritation and instability resulting from severe disc damage have largely focused on removal of the damaged disc and fusing the adjacent vertebral elements together. Removal of the disc relieves the mechanical and chemical irritation of neural elements, while osseous union (bone knitting) solves the problem of instability.

While cancellous bone appears ideal to provide the biologic components necessary for osseous union to occur, it does not initially have the strength to resist the tremendous forces that may occur in the intervertebral disc space, nor does it have the capacity to adequately stabilize the spine until long term bony union occurs. For these reasons, may spinal surgeons have found that interbody fusion using bone alone has an unacceptably high rate of bone graft migration or even expulsion or nonunion due to structural failure of the bone or residual degrees of motion that retard or prohibit bony union. Intervertebral prostheses in various forms have therefore been used to provide immediate stability and to protect and preserve an environment that fosters growth of grafted bone such that a structurally significant bony fusion can occur.

U.S. Pat. No. 5,505,732, No. 5,653,762, No. 5,665,122, and No. 5,683,463 describe different prior spinal implants. The implant shown in U.S. Pat. No. 5,483,463 is hollow and tubular, with communicating windows in the top and bottom surfaces. External ribs, which may be serrated, stabilize the implant once it is inserted between the vertebrae. In U.S. Pat. No. 5,665,122, an intervertebral cage is rendered expandable by a wedging mechanism. The degree of expansion is rather limited, however. U.S. Pat. Nos. 5,653,762 and 5,505,732 show shaft-type tools used for installing implants. The prior devices do not enable one to achieve great ranges of implant height, or to adjust taper angle for kyphotic and lordotic situations.

Limitations of most present-day intervertebral implants are significant and revolve largely around the marked variation in disc space shape and height that results from either biologic variability or pathologic change. For example, if a disc space is 20 mm in height, a circular implant bridging this gap requires a minimum diameter of 20 mm just to contact the end plate of the vertebral bone. Generally, end plate disruption must occur to allow a generous bony union, meaning that an additional 2–3 mm must be added on either end, resulting in a final implant size of 24–26 mm. During implantation from an anterior approach (from the front of the body), excessive retraction (pulling) is often required on the great blood vessels which greatly enhances the risk of devastating complications such as vascular tears or thrombosis. On the other hand, during a posterior approach, large implant diameters may require excessive traction on neural elements for adequate placement, even if all posterior bony elements are removed. In some instances, an adequate implant size cannot be inserted posteriorly, particularly if there is a significant degree of ligamentous laxity requiring higher degrees of distraction to obtain stability by tautening the annular ligamentous tension band. Compromising on implant size risks sub-optimal stability or a loose implant, which has a greater chance for migration within or expulsion from the disc space. The alternative of excessively retracting neural elements to facilitate a posterior implant application results in a neuropraxia at best and permanent neural damage at worst.

SUMMARY OF THE INVENTION

It is the object of this invention to provide an expandable intervertebral fusion implant that is both simple to manufacture and simple to use in daily clinical surgical practice while remaining versatile enough to address the complex biologic and pathologic variability of the human spine.

It is also intended that this device be applicable to all generally accepted surgical approaches to the spine, including microsurgical and endoscopic applications.

To achieve these objectives, a pair of metal shells are distracted inside an intervertebral space that has been appropriately prepared for fusion. An expansible installation tool is used to achieve optimal distraction, and the shells are held apart by teeth on legs which extend from semicylindrical bases. These legs preferably are curved to facilitate differential expansion of one end of the implant relative to the other to account for normal variations in the angle of the adjacent end plates; i.e., to preserve or enhance the lordotic or kyphotic attitude of adjacent vertebral body elements that are to be fused. The installation tool is then unscrewed and disengaged, leaving the component parts as a stable assembly that can be packed with bone to promote osseous union.

The present invention not only provides an expandable intervertebral fusion implant, but also lends itself readily to use in anterior, lateral and posterior approaches. In addition, one can insert devices of different sizes or angulations in a single intervertebral space to address lateral differences in disc space height to account for degrees of scoliosis, lordosis or kyphosis.

The tubular implant approximates a cylinder that is larger at one end and divided into cranial (upper) and caudal (lower) shells that contact the end plates of the vertebral bones above and below and can be distracted, or spread apart, by a screw-type installation tool until optimal distraction of the vertebral elements and appropriate tension on the ligamentous structures is achieved.

The larger end has corrugations or meshing teeth that interact in an arcuate fashion. The smaller end is secured by side rivets which permit arcuate expansion of the larger end. The installation tool is then retracted, allowing the two components to seat against one another and lock together, and the tool is then removed. The implant assembly is now packed with allograft or auto graft bone to allow long term bony union to develop between the vertebral elements.

The advantages provided by this invention include (1) the fact that both the tool and the implant components are of simple manufacture and (2) because of its expandable nature, this implant has the potential for use in microsurgical laminotomy, where only a small opening is made in the spine, resulting in minimal retraction of neural structures and maximizing preservation of posterior bony and ligaments spinal elements, and (3) lordotic and kyphotic orientations in the spine can be addressed. Most existing posterior interbody approaches require extensive bone removal to achieve spinal fusion whether or not an implant is used.

BRIEF DESCRIPTION OF THE DRAWINGS

In the accompanying drawings.

DESCRIPTION OF THE PREFERRED EMBODIMENT

Figure 1:
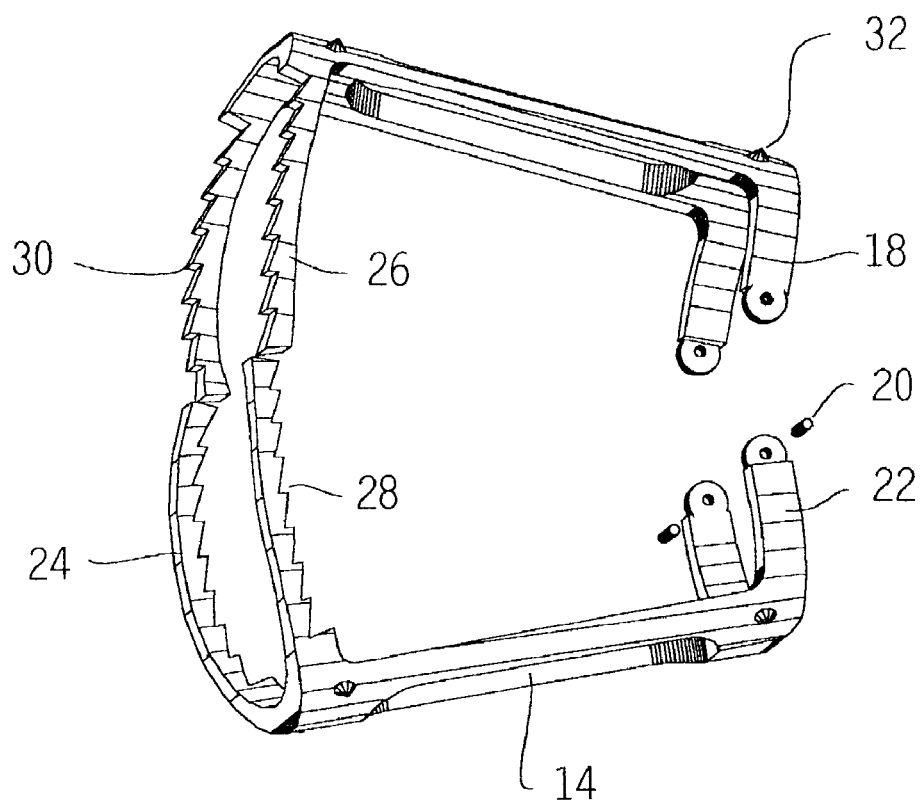
FIG. 1 is an exploded perspective view of a pair of shells forming an implant according to the invention.
Figure 2:
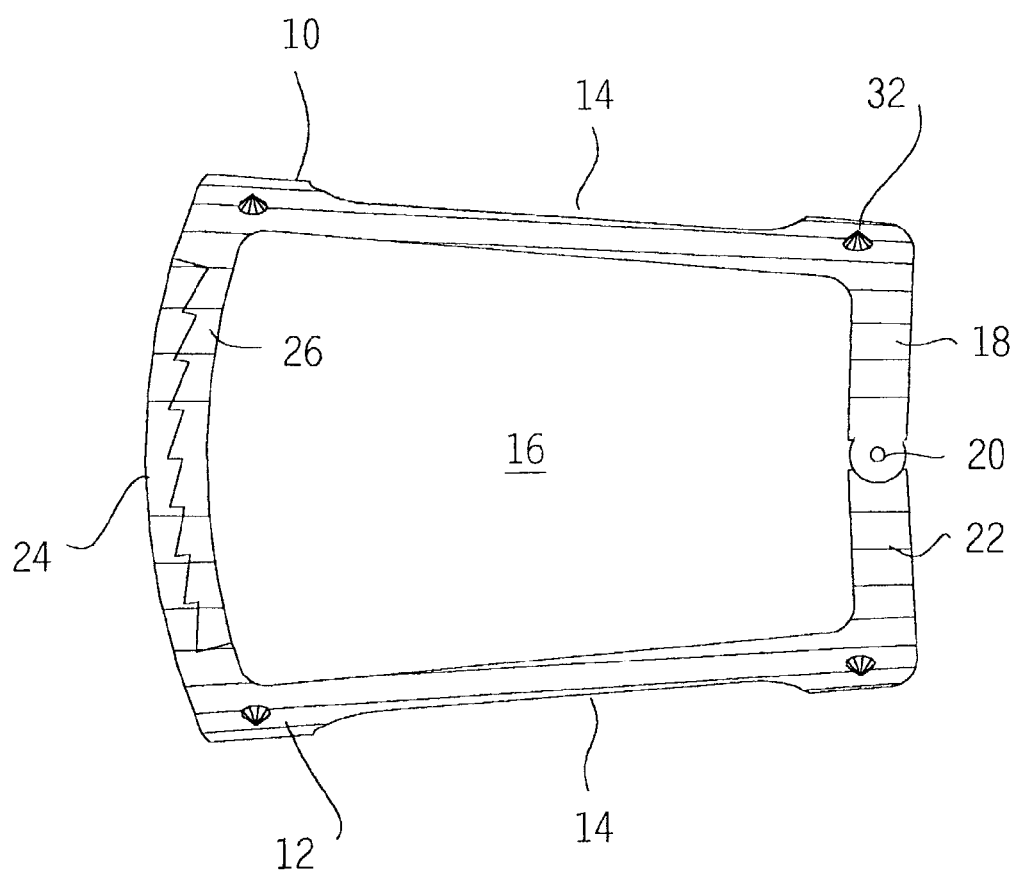
FIG. 2 is a side elevation, showing the shells assembled in a collapsed configuration.
Figure 3:
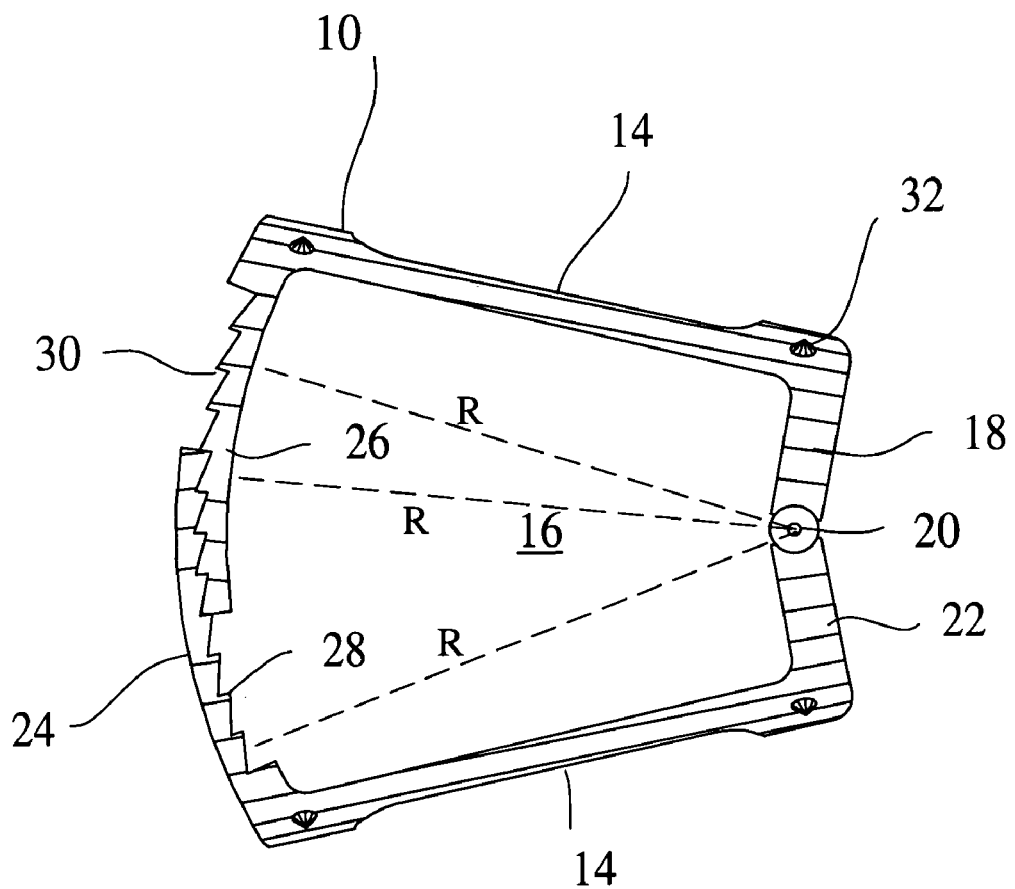
FIG. 3 is a view like FIG. 2, showing the shells expanded between adjacent vertebral elements.

An expandable intervertebral fusion implant embodying the invention appears in FIGS. 1–3. The implant comprises a pair of mating metal shells 10, 12. Each shell is generally sermicylindrical or, more accurately, semi-frustoconical. The vertical and horizontal bone growth windows 14, 16 define four legs on each shell: the two shorter legs 18 on the upper shell 10 are connected by hinge pins 20 to the opposite legs 22 on the lower shell 12. The longer legs 24 on the lower shell overlap those 26 on the upper shell, and these legs have teeth 28, 30 on their overlapping surfaces. The teeth are raked in opposite directions, to permit expansion of the shells by a surgeon, but to prevent unintended collapse thereafter. The ratcheting action also provides useful tactile or audible feedback to the surgeon. In one embodiment of the invention, each of the teeth 28, 30 on each of their respective legs 24, 26 are equidistant (for example, distances R in FIG. 3) from the hinge pins 20.

The shells may be made of the same material, or different materials. Suitable materials include stainless steel, titanium, ceramic, graphite, and various plastics and composites of the foregoing. The selection of material may affect the dimensions or proportions of the parts somewhat, but is generally a matter of design choice.

To install an implant, the implant, in its fully collapsed configuration, is placed in the selected empty intervertebral space by means of an expandable tool (not shown). The jaws of the tools are then spread apart, forcing the shells outward into contact with the bones above and below. The points 32 on the shells dig into the bony material somewhat. Once the jaws are retracted, the tool can be removed from the site, and the implant remains expanded.

It may be appreciated that changes in geometry and materials may be made to the elements of the invention while retaining their essential function. For example, the hinges may be pivot connection other than pin-type connections: they could even be continuous "living" hinges. The ratcheting mechanism could be a functional equivalent of the teeth illustrated. Finally, the overall shape of the device, and that of the bone growth windows, may be varied to suit the situation.

Since the invention is subject to modifications and variations, it is intended that the foregoing description and the accompanying drawings shall be interpreted as only illustrative of the invention defined by the following claims.

I claim:

1. An expandable intervertebral fusion implant for installation between two vertebrae, the implant comprising:
   a pair of shells, a hinge connection, having a pivot axis, pivotally connecting the two shells at one end thereof, and a ratcheting connection at the opposite end thereof which permits the shells to be spread apart, but prevents collapse thereafter, each shell having a vertebral support surface adapted to engage a respective one of the vertebrae, a first pair of legs, and a second pair of legs, the pairs of legs each projecting from the vertebral support surface toward the other one of the pair of shells, and the first pairs of legs forming said hinge connection wherein the second pair legs forms said ratchet connection.

2. The invention of claim 1, wherein the shells have substantially frustoconical surfaces.

3. The invention of claim 1, wherein each of said shells has at least one point extending therefrom for engaging an end plate of a vertebral element to stabilize the position of the implant.

4. The invention of claim 1, wherein the ratcheting connection comprises a plurality of teeth on one of the shells that are equidistant from said pivot axis.

5. The invention of claim 2, wherein the ratcheting connection comprises a plurality of teeth on one of the shells that are equidistant from said pivot axis.

6. The invention of claim 1, wherein the hinge connection comprises a pin to attach the first shell to the second shell.

7. The invention of claim 1, wherein the pivot axis is generally parallel to each of the vertebral support surfaces.

8. An expandable intervertebral fusion implant comprising:
   discrete first and second shells, each having a vertebral support surface;

a hinge connection, having a pivot axis generally parallel to each of the vertebral support surfaces, pivotally connecting the two discrete shells at a first end of the shells; and each shell having a first pair of legs extending from the vertebral support surface, the hinge connect being formed between the first pair of legs of the first shell and the first pair of legs of the second shell; and a ratcheting connection between the two shells at a second end of the shells, the ratcheting connection including a first surface portion extending from the first shell and having a first plurality of teeth, and a second surface portion extending from the second shell and having a second plurality of teeth, the first and second surface portions overlapping each other, the first plurality of teeth opposing the second plurality of teeth, permitting the shells to be spread apart, but preventing unintended collapse thereafter, and each shell further comprising a second pair of legs extending from the vertebral support surface, wherein the ratchet connection is formed between the second pair of legs of the first shell and the second pair of legs of the second shell.

9. The invention of claim 8, wherein the teeth on the respective shells are raked in opposite directions to permit shells to be only spread apart.

10. The invention of claim 8, wherein all of said first plurality of teeth are equidistant from said pivot axis.

11. The invention of claim 8, wherein all of said first plurality of teeth are equidistant from said pivot axis.

12. The invention of claim 8, wherein the hinge connection comprises a pin to attach the first shell to the second shell.

13. The invention of claim 8, wherein each of the shells has a substantially frustocornical surface.

14. The invention of claim 8, wherein each of said shells has at least one point extending therefrom for engaging an end plate of a vertebral element to stabilize the position of the implant.

* * * * *